United States Patent [19]
Wang

[11] Patent Number: 6,083,482
[45] Date of Patent: Jul. 4, 2000

[54] CONFORMATIONALLY LOCKED NUCLEOSIDES AND OLIGONUCLEOTIDES

[75] Inventor: Guangyi Wang, Irvine, Calif.

[73] Assignee: ICN Pharmaceuticals, Inc.

[21] Appl. No.: 09/309,742

[22] Filed: May 11, 1999

[51] Int. Cl.$^7$ .......................... C07H 21/02; C07H 21/04; C12P 19/34
[52] U.S. Cl. ........................ 424/1.73; 536/22.1; 536/23.1; 536/25.6; 435/91.1
[58] Field of Search .................................. 536/23.1, 22.1; 424/1.73; 435/91.1

[56] References Cited

PUBLICATIONS

Guangyi Wang, Conformationally locked nucleosides. Synthesis and stereochemical assignments of 3'–N,5'–C–bridged 3'–amino–3'–deoxythymidines. Tetrahedron Letters 40 (1999), pp. 6343–6346, Oct. 1999.

*Primary Examiner*—George C. Elliott
*Assistant Examiner*—Janet L. Epps
*Attorney, Agent, or Firm*—Fish & Associates, LLP; Robert D. Fish

[57] ABSTRACT

Conformationally restricted 3',5'-bridged nucleoside analogues are described herein. The compounds can be prepared by cyclization at C3' and C5' of nucleosides through a linker or linking molecule. The nucleoside bases may be modified or unmodified. The nucleosides can be used as oligonucleotide building blocks or as small molecule pharmaceutical ingredients.

7 Claims, No Drawings

CONFORMATIONALLY LOCKED NUCLEOSIDES AND OLIGONUCLEOTIDES

FIELD OF THE INVENTION

The field of the invention is nucleoside and oligonucleotide analogues and methods for their preparation.

BACKGROUND

Sugar-modified nucleoside analogues such as 3'-azido-3'-deoxythymidine and 2'3'-dideoxynucleosides have been used as transcription inhibitors for a variety of viral infections. Recently, certain nucleoside analogues built on a bicyclic sugar, 3'-endo 4',6'-methanocarbocyclic nucleosides, demonstrated potent activity against HSV, HMCV, and EBV. The AZT TP analogue of the 4',6'-methanocarbocyclic thymidine is an equipotent inhibitor of HIV reverse transcriptase as is AZT (Marquez et al. *J. Med. Chem.* 1996, 39, 3739–3747; 1998, 20, 2780–2789).

A number of other bicyclic-sugar nucleosides have also been reported. Unfortunately, these nucleosides showed either no or weak biological activity. Apparently, each type of bicyclic-sugar moiety has a unique geometrical shape, and a unique interaction pattern with biological targets. Bicyclic-sugar nucleosides could be useful as antiviral compounds, but to date have not been intensively explored.

In addition to the utility as pharmaceutical ingredients, nucleoside analogues built on bicyclic-sugar moieties can be useful as building blocks for oligonucleotides. Oligonucleotides are known to sequence-specifically bind to DNA and RNA, therefore, they can be potentially useful as antisense inhibitors of gene expression or as gene probes.

A molecule can be "locked" into desired conformation by chemically adding a molecular bridge onto the molecule. The conformationally-modified nucleosides can then be used to form conformationally-modified oligonucleotides that have certain desired, geometrical shapes and entropy advantages over unmodified nucleosides. Among known bicyclic-sugar modified oligonucleotides, those containing 2',4'-bridged nucleosides demonstrate excellent hybridization to complementary DNA and RNA (Koshkin et al. *Tetrahedron* 1998, 54, 3607–3630; Wang et al. *Bioorg. Med. Chem. Lett.* 1999, 9, 1147–1150).

In addition to sugar-modified oligonucleotides, tremendous efforts have been made to explore backbone-modified oligonucleotides. It appears that both favorable sugar and backbone modifications can enhance oligonucleotides' potential as antisense therapeutics or as gene-specific diagnostics.

The present invention describes a combination of favorable backbones and conformationally locked, 3'-endo sugar moieties in nucleosides and oligonucleotides. The effects from the conformationally locked sugar and the modified, favorable backbones can be synergetic, therefore, the oligonucleotides containing these modifications can have superior hybridization to DNA or RNA, as well as excellent biological stability.

SUMMARY OF THE INVENTION

The present invention provides bicyclic-sugar nucleosides having the formula I

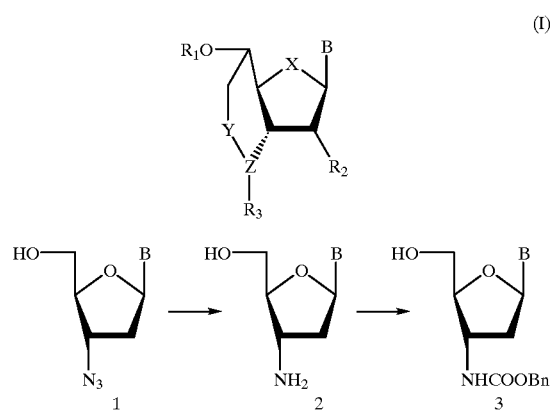

wherein

B is selected from a group comprising adenine, cytosine, guanine, hypoxanthine, uracil, thymine, a nucleoside base, or a modified nucleoside base;

X and Y are independently selected from a group comprising $O$, $S$, $CH_2$, $C=O$, $C=S$, $C=CH_2$, $CHF$, $CF_2$;

Z is selected from N, CH;

$R_2$ is H, F, OH, or OMe;

$R_1$, $R_3$ is independently selected from H, OH, $P(OR)_2$, $P(O)(OR)_2$, $P(S)(OR)_2$, $P(O)(SR)OR$, acyl, carbobenzoxy, trifluoroacetyl, p-nitrophenyloxycarbonyl, or any suitable protecting group or activating group for building oligomers, where R is H, 2-cyanoethyl, diisopropylamino, alkyl, alkenyl, alkynyl, or a hydrophobic masking group. R can be the same or different from one another in case of $(OR)_2$, $(SR)OR$.

The present invention also provides bicyclic-sugar nucleoside dimers (dimer being used in the following context) having the formula II and III comprising at least one aforementioned bicyclic-sugar nucleosides according to formula I

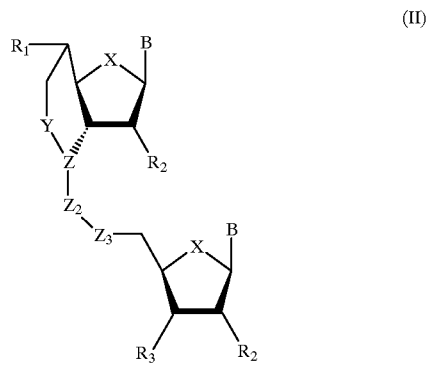

-continued

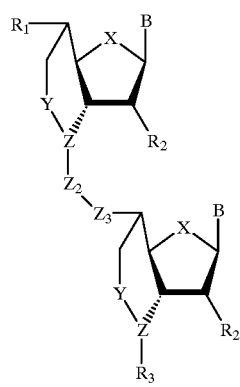

(III)

wherein $Z_2$ and $Z_3$ are independently selected from O, S, CO, P(O), P(O)O, $CH_2$; $R_1$ and $R_3$ are independently selected from OH, NH, $NH_2$, DMTO, TBDMSO, OP(OR) $N(iPr)_2$, OP(OR)(O)H, in which R can be methyl or 2-cyanoethyl.

The present invention also comprises oligomers containing at least one bicyclic-sugar nucleoside or dimer according to formulas I, II, or III. Processes are also provided for preparation of bicyclic-sugar nucleosides, dimers, and oligomers according to formula I, II, or III.

The term "Bicyclic-sugar nucleoside" refers to the nucleoside analogue having a modified sugar in which a linker connects C3' and C5' of the ribose or deoxyribose.

The term "Alkyl" refers to a C1–C20 aliphatic substituent, normal or branched. The term "Alkenyl" refers to a C1–C20 aliphatic substituent, normal or branched, containing at least one carbon-carbon double bond. The term "Alkynyl" refers to a C1–C20 aliphatic substituent, normal or branched, containing at least one carbon-carbon triple bond. The term "Aralkyl" refers to a combination of aromatic rings and the aforementioned alkyl, alkenyl, and alkynyl groups. The term "hydrophobic masking group" refers to one or more alkyl, alkenyl, alkylnyl, or aralkyl substituents, which are attached to the aforementioned functional groups and can function as a prodrug.

The term "DMT" refers to 4,4'-dimethoxytrityl. The term "TBDMS" refers to t-butyldimethylsilyl. The term "DMAP" refers to 4-dimethylaminopyridine. The term "DCC" refers to dicyclohexylcarbodiimide. The term "TFA" refers to trifluoroacetic acid. The term "TBAF" refers to tetrabutylammonium fluoride.

DETAILED DESCRIPTION OF THE INVENTION

Bicyclic-sugar nucleosides which are conformationally restricted and which have a common geometrical shape are described. Bicyclic-sugar nucelosides described herein can be either linked to one another or linked to another modified or unmodified nucleoside through a number of biologically and chemically stable backbones, such as phosphoramidate, carbamate, amide, phosphonate, tertiary amine, oxyamine.

Synthesis of Bicyclic-Sugar Nucleosides

3'-amino-3'-deoxynuceosides are useful precursors in the synthesis of 3'-C-amino-3'-deoxy-5'-O-(4,4'-dimethoxytrityl)-5'(R)-C,3'-N-ethano nucleosides. 3'-amino-3'-deoxynuceosides can be prepared according to previously published procedures (Chen et al. *Nucleic Acids Res.* 1995, 23, 2661–2668; Gryaznov, et al. *Nucleic Acids Res.* 1998, 26, 4160–4167). The procedures for preparation of bicyclic-sugar thymidine analogues (B=thymine) are described herein. Other bicyclic-sugar nucleosides can be similarly prepared in the same way. 3'-Azido-3'-deoxythymidine 1 prepared according to a published procedure (Czernecki et al. *Synthesis* 1991, 239–240) can be hydrogenolyzed over Pd/C to give 3'-amino-3'-deoxythymidine 2. 3'-amino-3'-deoxythymidine can be, in turn, reacted with benzyl chloroformate to produce compound 3 as shown below.

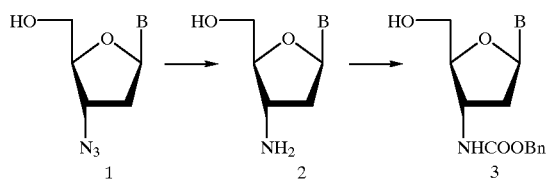

The 5'-hydroxyl component of the compound 3 can be oxidized 3'-amino-3'-deoxythymidine to an aldehyde, as shown by compound 4, which can be subjected to Reformatsky reaction with ethyl bromoacetate and zinc to produce compounds 5 and 6, a pair of isomers, as shown below.

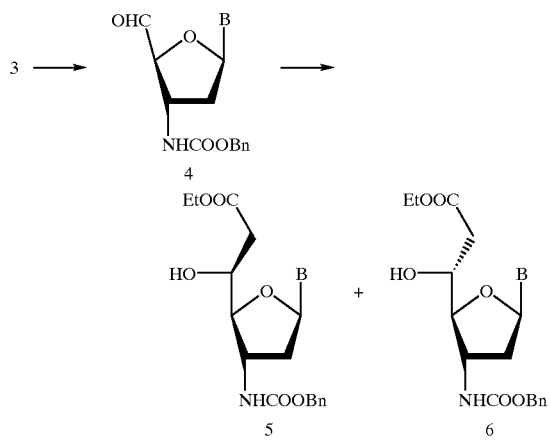

Compounds 5 and 6 can be separated by chromatography on silica gel. Separated compounds 5 and 6 can be reacted with 4,4'-dimethoxytrityl chloride in the presence of silver nitrate to produce compounds 7 and 8, respectively, as shown below, or a mixture of compounds 7 and 8 can be prepared from a mixture of compounds 5 and 6.

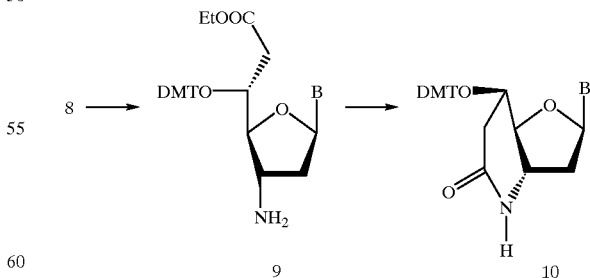

Compound 8 (wherein R=DMT) can be subjected to hydrogenolysis over Pd/C to produce an intermediate 9, in which the resulting amino group attacked the intramolecular ethyl ester substituent to produce the bicyclic compound 10 as shown below.

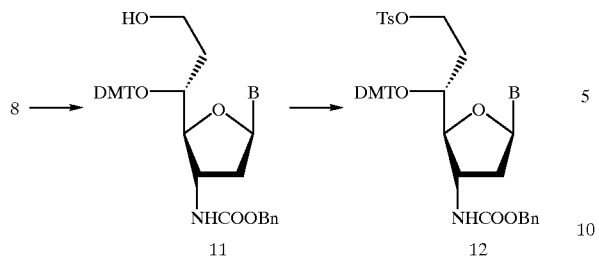

Treatment of compound 8 with lithium aluminum hydride reduces the 5'-ethoxycarbonylmethyl to a hydroxyethyl group to produce compound 11, which can be further converted to p-toluenesulfonate 12.

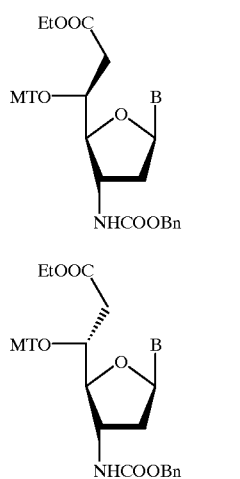

Compound 12 can be hydrogenolyzed over Pd/C to yield an intermediate 13, in which an intramolecular cyclization takes place to produce compound 14.

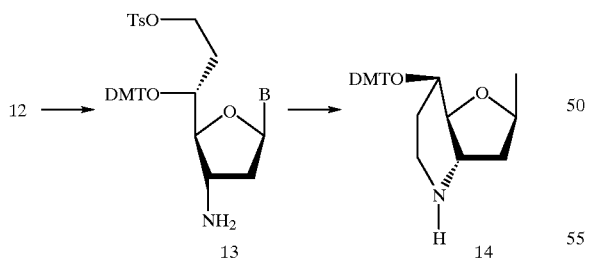

Compound 11 can be subjected to hydrogenolysis to produce compound 15, which can be further reacted with fluorenylmethyl N-succinimidyl carbonate to produce compound 16. Mesylation of 16 results in the formation of compound 17, which can be treated with DMAP to remove the Fomc group. The released amino can then attack the sulfonate substituent to produce compound 14. This approach is an alternative to hydrogenolysis.

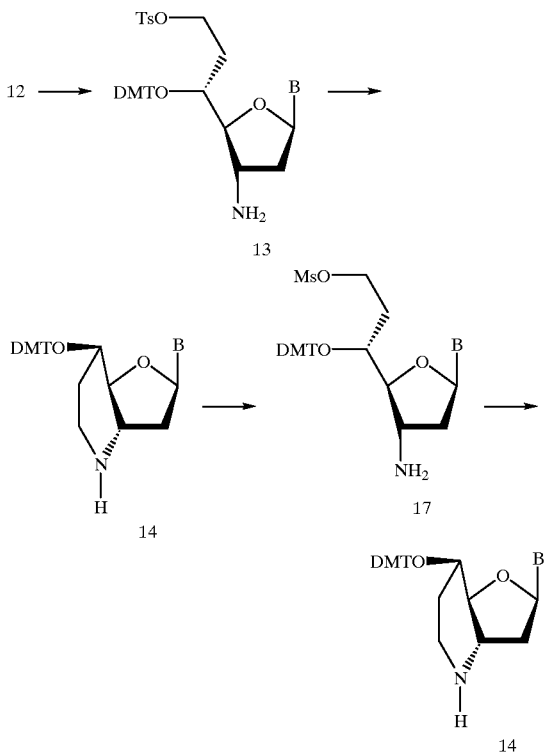

Compounds 10 and 14 can be treated with 80% acetic acid to produce compounds 18 and 19, respectively, which can be potentially useful as small molecular inhibitors. Compound 18 can be reacted with benzyl chloroformate, and the resulting intermediate can be treated with methanesulfonyl chloride to produce a 5'-O-mesyl derivative 20. Compound 20 and its 5'(S)-isomer (not shown) were subsequently used in NOE nuclear magnetic resonance experiments to determine the stereochemistry of the bicyclic-sugar nucleosides.

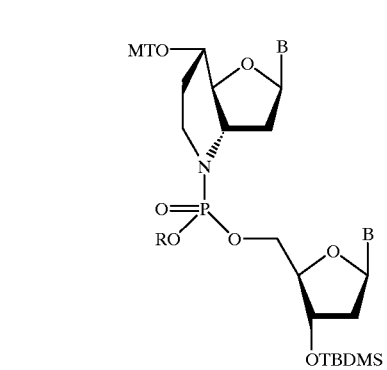

Synthesis of Bicyclic-Sugar Nucleoside Dimers

Bicyclic-sugar nucleoside dimers can be used for oligonucleotide synthesis in the same way as unmodified nucleosides. The phosphoramidate dimers can be prepared from condensation of compound 14 with 5'-O-hydrogen phosphonyl nucleosides. In the case of thymidine derivative, the condensation of 14 with 3'-O-(t-butyldimethylsilyl)-5'-O-hydrogen phosphonylthymidine produced compound 21 as shown below, wherein R can be either methyl or 2-cyanoethyl.

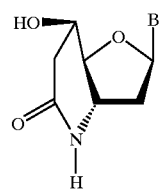

18

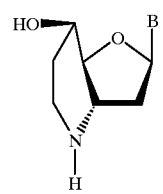

19

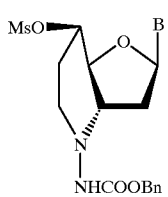

20

Carbonate backbone dimers can be prepared from 14 and 5'-O-(p-nitrophenyloxycarbonyl)nucleosides. In the case of thymidine derivative, compound 22 can be prepared from the condensation of 14 with 3'-O-(t-butyldimethylsilyl)-5' (p-nitrophenyloxycarbonylthymidine. 3'-O-(t-butyldimethylsilyl)-5'(p-nitrophenyloxycarbonylthymidine can be prepared from reaction of 3'-(t-butyldimethylsilyl) thymidine with p-nitrophenyl chloroformate.

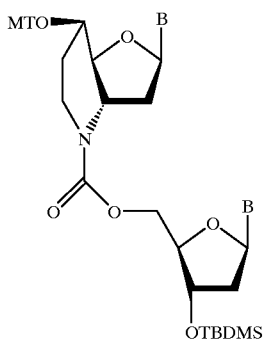

22

Cyclic-acyl phosphoramidate dimers 24, as shown below, can be prepared from compound 10 through a series of sequential reactions. Treatment of 10 with 2-cyanoethyl phosphoramidous dichloride can produce compound 23, which is reacted in one-pot reaction with 3'-(t-butyldimethylsilyl)thymidine. The resulting intermediate (not shown) can be oxidized with iodine to produce compound 24.

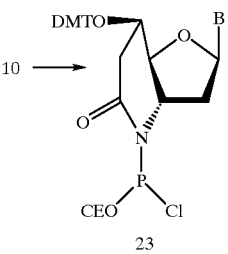 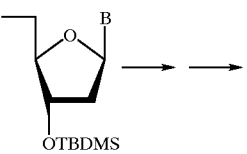

23

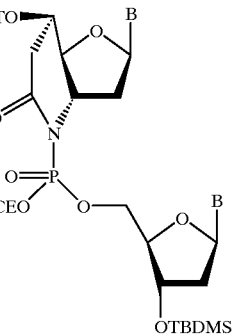

24

Treatment of dimers 21, 22, and 24 with tetrabutylammonium fluoride, followed by reaction with 2-cyanoethyl-N,N-diisopropylchlorophosphoramidite can produce 3'-O-(2-cyanoethyl-N,N-diisopropylphosphoramidite) substituents of dimers 25–27. Dimers 25–27 can be used in oligonucleotide synthesis by using a standard phosphoramidite approach.

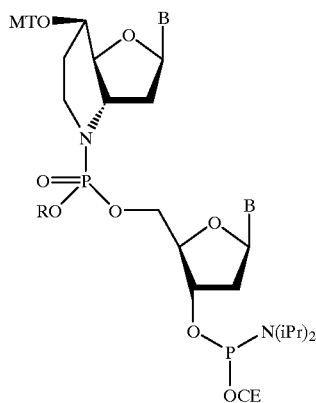

25

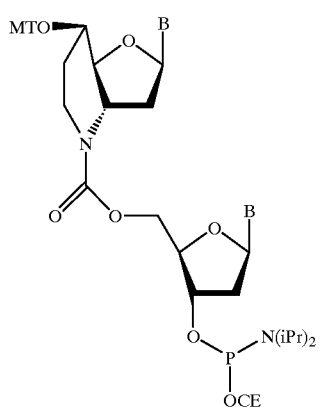

26

-continued

27

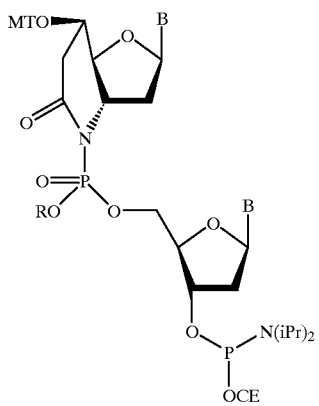

Synthesis of Oligomers Containing Bicyclic-Sugar Nucleosides

Synthesis of oligomers containing the bicyclic-sugar nucleosides can be prepared either through incorporation of the aforementioned nucleoside dimers by the standard oligonucleotide synthesis approach, or through the bicyclic-sugar nucleoside monomer by previously described procedures for N3-P5 backbone modifications (Chen et al. *Nucleic Acids Res.* 1995, 23, 2661–2668). The procedures used for preparation of dimer 21 can also be used for preparation of the oligomer.

EXAMPLES

The present invention is described below in detail using the following examples. The approach described is applicable to both bicyclic-sugar pyrimidine analogues and bicyclic-sugar purine nucleosides. The present invention includes, but is not limited to the following examples. In the examples, the compound names are followed by a number in bracket which corresponds to a structure in the detailed description section.

Example 1

Preparation of 3'-benzyloxycarbamido-3'-deoxythymidine (3)

A mixture of 3'-azido-3'-deoxythymidine (10 g, 37.45 mmol, Czernecki et al. *Synthesis* 1991, 239–240) and 10% palladium on charcoal (1.0 g, Aldrich, ~50% water) in methanol 200 mL) was shaken in a hydrogenation apparatus at room temperature under 55 psi hydrogen for 4 h. The catalyst was filtered and washed thoroughly with methanol. The filtrate was concentrated to dryness and the crude product dried under vacuum overnight. Additional 10 g of 3'-azido 3'-deoxythymidine was subjected to the same reaction. The products from the two reactions were combined and dissolved in an aqueous solution of sodium carbonate (7.95 g, 75 mmol) in 600 mL of water. The resulting solution was cooled with ice and benzyl chloroformate (112.7 mmol, 16.1 mL) was added dropwise. The resulting mixture was stirred at 0° C. for 1 h. The precipitate was filtered, washed with water, dried at 70° C. in a vacuum oven overnigh to give 27.54 g of the titled compound as a colorless solid. The filtrate was extracted with hexanes (200 mL), and then with chloroform (3×100 mL). The chloroform extracts were dried over sodium sulfate and concentrated to dryness. Crystallization from methylene chloride and hexanes gave additional 0.4 g of the titled compound. Total yield: 27.94 g (99%).

Example 2

Preparation of 3'-benzyloxycarbamido-3'-deoxy-5'-C,5'-O-didehydrothymidine (4)

To a stirred solution of 3'-benzyloxycarbamido-3'-deoxythymidine (27.90 g, 74.4 mmol) and DCC (30.70 g, 148.8 mmol) in anhydrous DMSO (200 mL) and ether (100 mL) at 0° C. under argon was added a solution of TFA (2.90 mL, 37.3 mmol) and pyridine (6.0 mL, 74.4 mmol) in DMSO (20 mL). The resulting mixture was stirred at room temperature for 5 h and then cooled with ice. Oxalic acid (13.5 g, 150 mmol) in 60 mL of methanol was added and the resulting mixture was stirred at 0° C. for 30 min and then at room temperature for 1 h. The precipitate was filtered and washed thoroughly with chloroform. The filtrate was washed with brine (5 times), dried (sodium sulfate), and concentrated to dryness. Chromatography on silica with 1.2% methanol in methylene chloride-ethyl acetate (1:1) gave 24.9 g (89.7%) of the titled compound as a colorless solid.

Example 3

Preparation of 3'-benzyloxycarbamido-3'-deoxy-5' (R,S)-C-ethoxycarbonylmethylthymidine (5 and 6)

To a stirred zinc powder (8.24 g, 126 mmol) in anhydrous THF (120 mL) under argon was added about one third of ethyl bromoacetate (13.3 mL, 120 mmol). The mixture was stirred at ambient temperature for several min and became warm and yellow colored. The rest of the reagent was added in portions to keep the reaction temperature below 50° C. The resulting yellow solution was stirred at ambient temperature for 20 min and 3'-benzyloxycarboamido-3'-deoxy-5'-C,5'-O-didehydrothymidine (7.46 g, 20.0 mmol) in THF (60 mL) was added. The reaction mixture was stirred at 45° C. for 20 h, cooled with ice, 10% AcOH added to quench the reaction. The mixture was diluted with ethyl acetate, washed with 10% AcOH twice, with water three times, then with 10% sodium bicarbonate, dried over sodium sulfate, and concentrated to dryness. Chromatography on silica with ethyl acetate-hexanes (3:1) gave 5.71 g (61.9%) of the titled compound as a colorless foam, which contained two isomers (ratio 1:1). The two isomers were partially separated by the chromatography.

Example 4

Preparation of 3'-C-benzyloxycarbamido-3'-deoxy-5'-O-(4,4'-dimethoxytrityl)-5'(R,S)-C-ethoxycarbonylmethylthymidine (7 and 8)

To a stirred solution of 3'-benzyloxycarbamido-3'-deoxy-5'(R,S)-C-ethoxycarbonylmethylthymidine (14.1 g, 30.58 mmol) and 4,4'-dimethoxytrityl chloride (41.45 g, 122.3 mmol) in anhydrous pyridine (90 mL) was added silver nitrate (20.79 g, 122.3 mmol) in portions. The resulting mixture was stirred at ambient temperature for 30 min then at 55° C. for 34 h, cooled with ice, diluted with ethyl acetate, washed with brine three times, dried over sodium sulfate, and concentrated to dryness. Chromatography on silica with ethyl acetate-hexanes (1:1 to 2:1) gave 21.2 g (91%) of the titled compound as a slightly yellow foam.

Example 5

Preparation of 3'-C-benzyloxycarbamido-3'-deoxy-5'-O-(4,4'-dimethoxytrityl)-5'(R)-C-hydroxyethylthymidine (11)

To a stirred suspension of lithium aluminum hydride (2.98 g, 78.38 mmol) in anhydrous THF (160 mL) at 0° C. under argon was added dropwise a solution of 3'-C-benzyloxycarbamido-3'-deoxy-5'-O-(4,4'-dimethoxytrityl)-5'(R,S)-C-ethoxycarbonyl methylthymidine (11.93 g, 15.67 mmol) in THF (60 mL) during 30 min. The reaction mixture was stirred at 0° C. for 1.5 h, then cooled with ice, and 10% sodium bicarbonate was added slowly to quench the reaction. The mixture was diluted with ethyl acetate, washed with 5% sodium bicarbonate three times, dried over sodium sulfate, and concentrated to dryness. Chromatography on silica with 4% ethanol in methylene chloride gave 4.83 g of 5'(R)-isomer and 4.61 g of 5'(S)-isomer, both as a colorless foam. Total yield of the titled compounds was 9.44 g (84%).

Example 6

Preparation of 3'-C-benzyloxycarbamido-3'-deoxy-5'-O-(4,4'-dimethoxytrityl)-5'(R)-C-(p-tosyloxy) ethylthymidine (12)

To a stirred solution of 3'-C-benzyloxycarbamido-3'-deoxy-5'-O-(4,4'-dimethoxy-trityl)-5'(R)-C-hydroxyethylthymidine (2.85 g, 3.95 mmol) and DMAP (443 mg, 3.95 mmol) in anhydrous pyridine (15 mL) was added in portions a solution of p-tosyl chloride (2.26 g, 11.85 mmol). The mixture was stirred at ambient temperature for 5 h, then cooled with ice, quenched with water (1.5 mL), and stirred at room temperature for 30 min, diluted with ethyl acetate, washed with 10% AcOH three times, with brine three times, then with 10% sodium bicarbonate, dried over sodium sulfate, and concentrated to dryness to give 3.28 g (94.9%) of the titled compound as a slightly pink foam, which was used directly without further purification.

Similarly, 3'-C-benzyloxycarbamido-3'-deoxy-5'-O-(4,4'-dimethoxytrityl)-5'(S)-C-(p-tosyloxy)ethylthymidine was prepared.

Example 7

Preparation of 3'-deoxy-5'-O-(4,4'-dimethoxytrityl)-3'-C-fluorenylmethoxy-carbamido-5'(R)-C-hydroxyethylthymidine (16)

3'-C-Benzyloxycarbamido-3'-deoxy-5'-O-(4,4'-dimethoxytrityl)-5'(R)-C-hydroxyethylthymidine (5.40 g, 7.49 mmol) in ethanol (250 mL) was subjected to hydrogenolysis over 10% Pd/C (1.0 g) under 50 psi hydrogen at room temperature for 30 h. The catalyst was filtered and washed with ethanol. The filtrate was concentrated to dryness to give 4.29 crude product as a foam, which was thoroughly dried under vacuum and dissolved in anhydrous THF (30 mL). To the stirred solution was added a solution of fluorenylmethyl N-succinimidyl carbonate (2.78 g, 8.24 mmol) in THF (30 mL), followed by addition of triethylamine (1.0 mL). The resulting mixture was stirred at room temperature for 1 h. The precipitate was filtered and washed with methylene chloride and toluene. The filtrate was concentrated and the residue chromatographed on silica with 4–10% ethanol in methylene chloride to give 2.67 g of the titled compound as a colorless solid.

Example 8

Preparation of 3'-deoxy-5'-O-(4,4'-dimethoxytrityl)-3'-C-fluorenylmethoxy-carbamido-5'(R)-C-mesyloxyethylthymidine (17)

To a stirred solution of 3'-deoxy-5'-O-(4,4'-dimethoxytrityl)-3'-C-fluorenylmethoxycarbamido-5'(R)-C-hydroxyethylthymidine (2.61 g, 2.87 mmol) in anhydrous pyridine (25 mL) at 0° C. was added dropwise mesyl chloride (0.48 mL, 5.76 mmol). The resulting solution was stirred at ambient temperature for 2 h, quenched by slowly adding water while cooled with ice, then stirred at room temperature for 30 min, diluted with ethyl acetate, washed with brine three times, dried over sodium sulfate, and concentrated. The residue was co-evaporated with toluene twice and dried under vacuum to give 3.17 g of the titled compound as a colorless foam.

Example 9

Preparation of 3'-C-amino-3'-deoxy-5'-O-(4,4'-dimethoxytrityl)-5'(R)-C,3'-N-ethanothymidine (14)

Method 1

A mixture of 3'-C-benzyloxycarbamido-3'-deoxy-5'-O-(4,4'-dimethoxytrityl)-5'(R)-C-(p-tosyloxy)ethylthymidine (1.06 g, 1.21 mmol), triethylamine (3.0 mL), and 10% palladium on charcoal (240 mg, Aldrich, ~50% water) in ethanol (180 mL) was shaken in a hydrogenation apparatus at room temperature under 50 psi hydrogen for 22 h. The catalyst was filtered and washed thoroughly with methanol. The filtrate was concentrated to dryness. The same scale reaction was repeated twice. The combined crude product was chromatographed on silica with 5% triethylamine and 4% ethanol in methylene chloride to give 1.51 g (72.9%) of the titled compound as a colorless foam.

Similarly, 3'-C-amino-3'-deoxy-5'-O-(4,4'-dimethoxytrityl)-5'(S)-C,3'-N-ethano-thymidine was prepared.

Method 2

A solution of 3'-deoxy-5'-O-(4,4'-dimethoxytrityl)-3'-C-fluorenylmethoxy-carbamido-5'(R)-C-mesyloxyethylthymidine (3.71 g, 2.87 mmol) and DMAP (9.0 g) in anhydrous THF (90 mL) stood at 40° C. for 20 h and was concentrated to dryness. Chromatography on silica with 4% ethanol in methylene chloride gave 1.04 g of the titled compound as a colorless foam, which is identical to the compound from Method 1, as evidenced by NMR and TLC.

Example 10

Preparation of 3'-C-amino-3'-deoxy-5'(R)-C,3'-N-ethanothymidine (19)

A solution of 3'-C-amino-3'-deoxy-5'-O-(4,4'-dimethoxytrityl)-5'(R)-C,3'-N-ethanothymidine (117 mg, 0.2 mmol) in 80% AcOH (5.0 mL) stood at 40° C. for 1 h. Solvent was evaporated and the residue chromatographed on silica with 5% triethylamine and 20% ethanol in methylene chloride to give 51 mg of the titled product as a slightly yellow solid.

Similarly, 3-C-amino-3'-deoxy-5'(S)-C,3'-N-ethanothymidine was prepared.

Example 11

Preparation of 3'-C-benzyloxycarbamido-3'-deoxy-5'(R)-C,3'-N-ethano-5'-O-mesylthymidine (20)

3'-C-Amino-3'-deoxy-5'(R)-C,3'-N-ethanothymidine (53 mg, 0.2 mmol) was dissolved in a solution of sodium carbonate (43 mg, 0.4 mmol) in water (1.5 mL). The resulting solution was cooled with ice and benzyl chloroformate (86 µL, 0.6 mmol) was added. The mixture was stirred at 0° C. for 30 min, diluted with 1,4-dioxane (0.5 mL), stirred at room temperature for 1 h, diluted with chloroform, washed with 10% sodium bicarbonate three times, dried over sodium sulfate, and concentrated to dryness. The residue was dissolved in anhydrous pyridine (0.5 mL) and mesyl chloride (77 mL, 1.0 mmol) was added at 0° C. The resulting solution was stirred at room temperature for 1 h, quenched by adding water (one drop), stirred at room temperature for 10 min. The mixture was diluted with chloroform, washed with dilute acetic acid, with water, then with 10% sodium bicarbonate, dried over sodium sulfate, and concentrated to dryness. Chromatography on silica with ethyl acetate-hexanes (3:1) gave 58 mg of the titled compound as a colorless solid.

Similarly, 3'-C-benzyloxycarbamido-3'-deoxy-5'(S)-C,3'-N-ethano-5'-O-mesyl thymidine was prepared, which together with 3'-C-benzyloxycarbamido-3'-deoxy-5'(R)-C, 3'-N-ethano-5'-O-mesylthymidine were used to determine the stereochemistry through NOE experiments.

Example 12

Preparation of 3'-O-(t-butyldimethylsilyl)-5'-O-(p-nitrophenyloxycarbonyl)thymidine p-Nitrophenyl chloroformate (252 mg, 1.25 mmol) in anhydrous methylene chloride was added to a stirred solution of 3'-O-(t-butyldimethylsilyl)thymidine (356 mg, 10 mmol, Wang et al. Nucleosides Nucleotides 1998, 17, 1033–1051) in anhydrous methylene chloride (4 mL) and pyridine (0.5 mL). The resulting solution was stirred at room temperature overnight, then cooled with ice, quenched with water (2 mL), stirred at 0° C. for 30 min, diluted with methylene chloride, washed with dilute acetic acid, water, then 5% sodium bicarbonate, dried over sodium sulfate, and concentrated to dryness. Chromatography on silica with ethyl acetate-hexanes (1:1 to 3:2) gave 505 mg of the titled compound as a colorless foam.

Example 13

Preparation of 3'-C-(3'-O-t-butyldimethylsilylthymidine-5'-O-carbamido)-3'-deoxy-5'-O-(4,4'-dimethoxytrityl)-5'(R)-C,3'-N-ethanothymidine (22)

3'-C-Amino-3'-deoxy-5'-O-(4,4'-dimethoxytrityl)-5'(R)-C,3'-N-ethanothymidine (285 mg, 0.5 mmol) and DMAP (62 mg, 0.5 mmol) in a flask under argon was cooled with ice and a solution of 3'-O-(t-butyldimethylsilyl)-5'-O-(p-nitrophenyloxycarbonyl)-thymidine (313 mg, 0.6 mmol) in anhydrous methylene chloride (5 mL) was added. The resulting solution stood at room temperature for 20 h, diluted with ethyl acetate, washed with dilute acetic acid, with water twice, then with 10% sodium bicarbonate, dried over sodium sulfate, and concentrated to dryness. The residue was dissolved in THF (6 mL) and 1.0 M TBAF in THF (2.0 mL) was added. The solution stood at room temperature for 1 h and concentrated at room temperature. Chromatography on silica with 8% ethanol in methylene chloride gave 380 mg of the titled compound (dimer) as a colorless foam.

Similarly, 3'-C-(3'-O-t-butyldimethylsilythymidine-5'-O-acrbamido)-3'-deoxy-5'-O-(4,4'-dimethoxytrityl)-5'(S)-C,3'-N-ethanothymidine was prepared.

Example 14

Preparation of 3'-C-(3'-O-t-butyldimethylsilylthymidine-5'-O-carbamido)-3'-deoxy-5'-O-(4,4'-dimethoxytrityl)-5'(R)-C,3'-N-ethanothymidine 3'-O-(2-cyanoethyl-N,N-diisopropylphosphoramidite) (26)

To a solution of 3'-C-(3'-O-t-butyldimethylsilylthymidine-5'-O-carbamido)-3'-deoxy-5'-O-(4,4'-dimethoxy-trityl)-5'(R)-C,3'-N-ethanothymidine (423 mg, 0.5 mmol) and diisopropylehtylamine (0.35 mL, 2.0 mmol) in anhydrous methylene chloride at 0° C. under argon was added dropwise 2-cyanoethyl-N,N-diisopropylchlorophosphoramidite (0.23 mL, 1.0 mmol). The resulting solution was stirred at ambient temperature for 1.5 h, diluted at 0° C. with ethyl acetate, washed with cold 5% sodium bicarbonate twice, dried over sodium sulfate, and concentrated to dryness at 25° C. Chromatography on silica with 5% triethylamine and 8% acetone in methylene chloride gave 458 mg (87%) of the titled compound as a colorless foam, which contained two diastereomers (ratio ~1:1).

Similarly, 3'-C-(3'-O-t-butyldimethylsilylthymidine-5'-O-carbamido)-3'-deoxy-5'-O-(4,4'-dimethoxytrityl)-5'(S)-C,3'-N-ethanothymidine 3'-O-(2-cyanoethyl-N,N-diisopropylphosphoramidite) was prepared.

Example 15

Preparation of 3'-(t-butyldimethylsilyl)thymidine 5'-O-(2-cyanoethyl-N,N-diisopropylphosphoramidite)

To a solution of 3'-(t-butyldimethylsilyl)thymidine (1.10 g, 3.09 mmol) and diisopropylehtylamine (1.40 mL, 6.18 mmol) in anhydrous methylene chloride at 0° C. under argon was added dropwise 2-cyanoethyl-N,N-diisopropylchlorophosphoramidite (2.15 mL, 12.36 mmol). The resulting solution was stirred at room temperature for 30 min, diluted at 0° C. with ethyl acetate, washed with cold 5% sodium bicarbonate twice, dried over sodium sulfate, and concentrated to dryness at 25° C. Chromatography on silica gel with triethylamine-ethyl acetate-hexanes (5:40:55) gave 1.25 g of the titled compound as a colorless foam, which contained two diastereomers (ratio ~1:1).

Example 16

Preparation of 3'-(t-butyldimethylsilyl)-5'-O-hydrogenphosphonylthymidine

To a solution of 3'-(t-butyldimethylsilyl)thymidine 5'-O-(2-cyanoethyl-N,N-diisopropylphosphoramidite) (395 mg, 0.72 mmol) in acetonitrile (3 mL) at 0° C. under argon was added dropwise 4.3 mL of 0.5 M tetrazole in acetonitrile-water (9:1). The resulting solution stood at room temperature for 20 min, diluted at 0° C. with ethyl acetate, washed with cold brine four times, with water twice, dried over sodium sulfate, and concentrated to dryness at 25° C. The thoroughly dried, titled compound weighed 330 mg as a colorless foam.

Example 17

Preparation of 3'-C-(3'-O-t-butyldimethylsilylthymidine-5'-O-(2-cyanoethylphosphoramidyl)-3'-deoxy-5'-O-(4,4'-dimethoxytrityl)-5'(R)-C,3'-N-ethanothymidine (21)

To a solution of 3'-C-amino-3'-deoxy-5'-O-(4,4'-dimethoxytrityl)-5'(R)-C,3'-N-ethanothymidine (72 mg, 0.126 mmol) and triethylamine (80 µL) in anhydrous acetonitrile (0.8 mL) at 0° C. under argon was added dropwise a solution of 3'-(t-butyldimethylsilyl)-5'-O-hydrogenphosphonylthymidine (180 mg, 0.38 mmol) in acetonitrile-methylene chloride (1:1, 1.6 mL). The resulting solution stood at room temperature for 3 h, diluted at 0° C. with methylene chloride, and stood at −15° C. overnight. Solvent was evaporated and the residue was chromatographed on silica gel with 6% ethanol in methylene chloride to give 41 mg of the tilted compound as a colorless foam.

Example 18

Preparation of 3'-deoxy-5'-O-(4,4'-dimethoxytrityl)-3'-C-formamido-5'(R,S)-C,3"-C-methanothymidine (10)

A mixture of 3'-C-benzyloxycarbamido-3'-deoxy-5'-O-(4,4'-dimethoxytrityl)-5'(R,S)-C- ethoxycarbonylmethylthymidine (382 mg, 0.5 mmol) and 10% palladium on charcoal (80 mg, Aldrich, ~50% water) in ethanol (60 mL) was shaken in a hydrogenation apparatus at room temperature under 50 psi hydrogen for 20 h. The catalyst was filtered and washed thoroughly with ethanol. The filtrate was concentrated to dryness to give 298 mg of the titled compound as a slightly yellow foam containing two diastereomer as shown by NMR.

Example 19

Preparation of 3'-deoxy-3'-C-formamido-5'(R,S)-C,3''-C-methanothymidine (18)

A solution of 3'-deoxy-5'-O-(4,4'-dimethoxytrityl)-3'-C-formamido-5'(R,S)-C,3'-C-methanothymidine (250 mg. 0.42 mmol) in 80% AcOH (10 mL) stood at 45 ° C. for 30 min and was concentrated to dryness. Water (20 mL) and methylene chloride (10 mL) were added and the mixture was stirred for 5 min. The aqueous phase was washed with methylene chloride twice, with ethyl acetate twice, concentrated to dryness. The residue was co-evaporated with ethanol twice to give 118 mg of the titled compound as a colorless foam, which contained two diastereomers.

Example 20

Preparation of Oligonucleotides Containing 3'-C-amino-5'(R)-C,3'-N-ethano-thymidine This example illustrates the use of 3'-C-(thymidine-5'-O-carbamido)-3'-deoxy-5'-O-(4,4'-dimethoxytrityl)-5'(R)-C,3'-N-ethanothymidine 3'-O-(2-cyanoethyl-N,N-diisopropylphosphoramidite) for the synthesis of an oligonucleotide (shown below) containing 3'-C-amino-5'(R)-C,3'-N-ethanothymidine (T*).

5'-d(ATCTCTCCGCT*TCCTTTC)-3'

In this sequence, A, C, G, and T represent the unmodified deoxyribonucleoside and T* represents 3'-C-amino-5'(R)-C, 3'-N-ethanothymidine. The oligonuceotide in this example was synthesized by ABI 394 DNA Synthesizer. All the nucleosides are incorporated by using phosphoramidite chemistry. Incorporation of dA, dC, dG, and T is carried out by using the standard DNA synthesis reagents and the standard procedure. Owing to the steric hindrance of branched substituent at C5' position of the modified nucleosides, incorporation of T* is carried out by using longer coupling time (5 minutes). After the synthesis the work-up of synthesized oligonucleotide follows the standard procedure. The crude oligonucleotide was purified by reverse phase C18 column on Beckman HPLC using TEAA buffer (pH 7.0) and acetonitrile as mobile phase. 53.5 ODs of the purified oligonucleotide were obtained.

Similarly, the following modified oligonucleotides containing 3'-C-amino-5'(R)-C,3'-N-ethanothymidine (T*) were synthesized.

1. 5'-d(T* T T* T T* T T* T T* T T* T T* T T)-3'

2. 5'-d(T T T T T T* T T* T T T T T T)-3'

3. 5'-d(T* T C C T G T C T G A T G G C T* T C)-3'

Similarly, the following modified oligonucleotides containing 3'-C-amino-5'(S)-C,3'-N-ethanothymidine (T*) have been synthesized:

1. 5'-d(T* T T* T T* T T* T T* T* T T* T T)-3'

2. 5'-d(T T T T T T* T T* T T T T T T)-3'

What is claimed is:

1. A compound having the formula I,

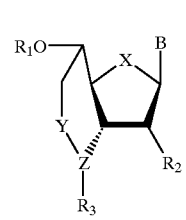

(I)

wherein
B is selected from a group comprising adenine, cytosine, guanine, hypoxanthine, uracil, thymine, a nucleoside base, or a modified nucleoside base;
X and Y are independently selected from a group comprising O, S, $CH_2$, C=O, C=S, $C=CH_2$, CHF, $CF_2$;
Z is selected from N, CH;
$R_2$ is H, F, OH, or OMe;
$R_1$ and $R_3$ are independently selected from H, OH, $P(OR)_2$, $P(O)(OR)_2$, $P(S)(OR)_2$, P(O)(SR)OR, acyl, carbobenzoxy, trifluoroacetyl, p-nitrophenyloxycarbonyl, or any suitable protecting group or an activating group for building oligomers, where R is H, 2-cyanoethyl, diisopropylamino, alkyl, alkenyl, alkynyl, or a hydrophobic masking group, where R can be same or different from each other in case of $(OR)_2$, $(SR)OR$.

2. The compound according to claim 1, wherein X is O; Y is C=O or $CH_2$; Z is N; $R_1$ and $R_3$ are hydrogen; and $R_2$ is H, or OH.

3. The compound according to claim 1, wherein X is O; Y is $CH_2$; Z is CH; and where $R_1$ $R_2$, and $R_3$ independently comprise H or OH.

4. A dimer having the formula II comprising at least one monomer according to any one of claims 1, 2 and 3;

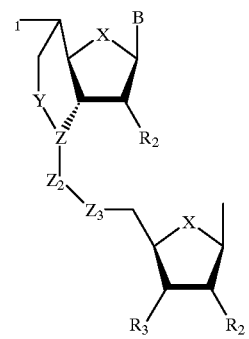

(II)

wherein $Z_2$ and $Z_3$ are independently selected from O, S, CO, P(O), P(O)R, P(O)O, $CH_2$; $R_1$ and $R_3$ are independently selected from OH, NH, $NH_2$, DMTO, TBDMSO, OP(OR) $N(iPr)_2$, OP(OR)(O)H; where R comprises methyl or 2-cyanoethyl.

5. A dimer having the formula III comprising at least two monomers according to any one of claims 1, 2, and 3

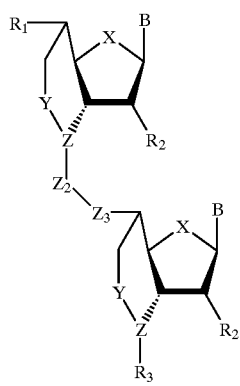
(III)
wherein $Z_2$ and $Z_3$ are independently selected from O, S, CO, P(O), P(O)R, P(O)O, $CH_2$; $R_1$ and $R_3$ are independently selected from OH, NH, $NH_2$, DMTO, TBDMSO, OP(OR)N(iPr)$_2$, OP(OR)(O)H; where R comprises methyl or 2-cyanoethyl.
6. An oligomer comprising at lest one monomer according to any one of claims 1, 2 and 3.
7. An oligomer comprising at least two monomers according to any one of claims 1, 2, and 3.
* * * * *